United States Patent [19]

Vistins

[11] Patent Number: 4,884,300
[45] Date of Patent: Dec. 5, 1989

[54] GLOVE HAVING IMPROVED CUFF SECURING FEATURES

[75] Inventor: Maris Vistins, Santa Cruz, Calif.
[73] Assignee: Becton, Dickinson and Company, Franklin Lakes, N.J.
[21] Appl. No.: 243,580
[22] Filed: Sep. 13, 1988
[51] Int. Cl.⁴ .......................................... A41D 19/00
[52] U.S. Cl. .......................................... 2/162; 2/160; 2/169
[58] Field of Search .............. 2/162, 159, 161 R, 166, 2/168, 123, 160, 169; 24/41, 42, 67 AR, 304, DIG. 11; 604/389; 15/227

[56] References Cited

U.S. PATENT DOCUMENTS

| Re. 31,538 | 3/1984 | Antonious | 2/161 A |
|---|---|---|---|
| 1,004,711 | 10/1911 | Tabor | 2/162 |
| 2,085,467 | 6/1937 | Lipton | 2/162 |
| 3,382,138 | 5/1968 | Barth | 428/423.9 |
| 3,555,564 | 1/1971 | Miskell et al. | 2/168 |
| 3,608,708 | 9/1971 | Storandt | 2/158 |
| 3,681,784 | 8/1972 | Lindley | 2/162 |
| 3,852,826 | 12/1974 | Schindler | 2/168 |
| 4,133,624 | 1/1979 | Heavner et al. | 425/275 |
| 4,345,597 | 8/1982 | Tritsch | 604/389 |
| 4,371,987 | 2/1983 | Brasfield | 2/162 |
| 4,434,126 | 2/1984 | McGary, Jr. et al. | 264/303 |
| 4,476,588 | 10/1984 | Long | 2/159 |
| 4,540,415 | 9/1985 | Korpman | 604/389 X |
| 4,677,697 | 7/1987 | Hayes | 2/159 |

FOREIGN PATENT DOCUMENTS

| 2196820 | 3/1974 | France | 15/221 |
|---|---|---|---|
| 255699 | 2/1949 | Switzerland | 2/159 |

Primary Examiner—Werner H. Schroeder
Assistant Examiner—Sara M. Current
Attorney, Agent, or Firm—John L. Voellmicke

[57] ABSTRACT

A disposable glove for medical use and the like includes a closed distal end for containing the wearer's fingers, an open proximal end, and a cuff portion at the open proximal end. Adhesive is provided on a portion of the cuff for allowing the portion of the cuff to be removably secured to other portions of the cuff for tightening the cuff when the glove is on the wearer's hand. A method of making the glove is also disclosed.

28 Claims, 4 Drawing Sheets

GLOVE HAVING IMPROVED CUFF SECURING FEATURES

BACKGROUND OF THE INVENTION

1. Field of the Invention

The present invention relates to gloves and more particularly concerns disposable gloves for medical uses, prevention of disease transfer and the like.

2. Description of Related Information

Disposable gloves have been used extensively by doctors, nurses, hospital employees and laboratory technicians for many years. These gloves are used for surgical procedures, medical examinations, treating patients having contagious diseases, blood drawing, testing and transfusions, and numerous other surgical, examination, medical and laboratory procedures. Due to the increased concern regarding diseases which may be transferred by contact from person to person, such as AIDS, gloves of this type are now being used by dentists, police officers, firefighting personnel, beauticians and even highway toll booth attendants.

Disposable gloves have been traditionally made of rubber material such as latex and thermoplastic materials such as vinyl. Latex gloves have been traditionally preferred by surgeons because of their high degree of elasticity which makes them more suitable for prolonged surgical procedures. Plastic gloves have traditionally been lower cost and well suited for routine examinations and many other tasks. Improvements in plastic technology are resulting in plastic gloves with physical properties similar to those of latex gloves so that it is no longer a hard and fast rule as to which type of glove material is more suitable for various procedures. However, all of the above-mentioned glove types, primarily because of their resilient properties and low thickness, have problems with respect to maintaining their position on the wrist of the wearer and folding down or rolling down during use.

A common method of making disposable gloves is by using a metal form in the shape of a human hand which during the manufacturing process is dipped with fingers facing downwardly, into a solution of material such as latex or plastisol which coats the form. The form is removed from the dip tank where it is subsequently subject to heat to promote curing or vulcanizing, or in the case of plastic, fusing into a glove which then may be stripped from the glove form. The art also teaches numerous other forming processes such as passing a heated glove form through a space containing fluidized finally divided particles of polyurethane polymer to produce a glove product as taught in U.S. Pat. No. 4,434,126 to McGary, Jr. et al.

Many of the attempts to eliminate or reduce glove roll down, as taught by the prior art, are achieved by additional steps in the glove forming process while the glove is still on the mold form. Hevner et al., in U.S. Pat. No. 4,133,624, provide a textured wrist portion to help eliminate glove roll down. Schindler, in U.S. Pat. No. 3,852,826, teaches a thin surgical glove provided with a colored circumferential band overlying the cuff portion to provide visual identification of the glove size and to further strengthen the cuff. The process of Schindler appears difficult to practice because the glove form must be dipped in a fingers down orientation, and then before curing, the form is partially immersed in a colored latex bath, in a fingers up orientation, wherein the desired width of band is deposited about the cuff portion. It has also been known that rolling the cuff downwardly before stripping the glove from the form will produce a stronger cuff structure which is believed to be less likely to roll down. In U.S. Pat. No. 4,371,987 Braisfield teaches a latex glove with an improved ring rolled cuff which comprises alternating tightly rolled segments with loosely rolled segments.

The problem of roll down is more difficult to solve with gloves made of thermoplastic materials. This is primarily due to the hand-shaped form which, like the human hand, has a circumference substantially smaller at the wrist portion than further down the form toward the fingertips. Because the molded glove is removed from the mold by stripping the glove cuff section down over the larger portion of the form, a permanent deformation of the plastic material may occur in the cuff area. On a large size glove, for example, a cuff roll molded to a diameter of two and one-half inches may be close to a permanent three inch diameter after stripping from the mold form.

After donning, a glove having a loose fit in the cuff section allows an opportunity for foreign materials to gain entrance to the glove interior thus compromising the amount of protection the glove can provide. In addition, a sloppy glove cuff may tend to fall down the wearer's wrist, reducing protection and presenting an opportunity to be inadvertently stripped from the user's hand during active use. Conversely, an overly tight cuff roll fit such as can be produced by a conventional rubber glove or rubber band inserted in the cuff roll of a plastic glove, may not be desirable either. With its high elastic memory, such a glove could not only cause difficulty in donning but provide increasingly undesirable effects to the user due to possible blood circulation restriction. A glove when worn must be such that it will not impair circulation in the wrist area because such impairment may affect the touch or tactile sense of the hand and the sensitivity of the hand to heat and cold and could possibly provoke hand and finger numbness when worn for a prolonged amount of time such as in a surgical procedure.

The prior art also teaches methods of providing a tighter cuff fit on reusable gloves such as gloves used in athletic competitions where a secure cuff fit is desirable. Typically, these sports gloves have numerous slits or openings which allow the glove to be easily placed on the user's hand and then the cuff portion is usually secured by a strap-like structure having a removable securing device such as Velcro-type fastening material. An example of sports gloves is taught in U.S. Pat. No. Re. 31,538 to Antonious. Gloves of this type are not suitable for medical procedures and the like because of the numerous vents and openings reguired by the design and the high cost of the securing means such as Velcro straps or belt and buckle-type straps.

Numerous solutions to the problem of loose cuffs and cuff roll-down in gloves have been taught by the prior art. However, there is still a need for a simple, straight-forward, reliable, easily fabricated disposable glove for medical use and the like having structure for removably securing the cuff portion of a disposable glove on the hand of the wearer during use without the glove being overly tight or difficult to donn properly. There is also a need for a disposable glove for medical use and the like wherein the fit in the cuff area may be adjusted to suit a wide variety of hand and wrist sizes.

SUMMARY OF THE INVENTION

The disposable glove for medical use and the like of the present invention comprises a closed distal end for containing the wearer's fingers, an open proximal end, and a cuff at the open proximal end. Adhesive means on a portion of the cuff allows that portion of the cuff to be removably secured to other portions of the cuff for tightening the cuff when the glove is on the wearer's hand.

In a preferred embodiment of the present invention, a disposable glove for medical use and the like comprises a hollow flexible body member having an interior surface and an exterior surface. The body member includes a closed distal end for containing the wearer's fingers, an open proximal end and a cuff at the open proximal end. Adhesive means is provided on a portion of the cuff for allowing the portion of the cuff to be removably secured to other portions of the cuff. A removable release sheet covers the adhesive means for protecting the adhesive means before time of use. The adhesive means is positioned so that when the glove is properly positioned on the wearer's hand the cuff, with release sheet removed from the adhesive means, may be circumferentially gathered in a direction substantially tangent to the open proximal end causing the adhesive means to press against another portion of the cuff removably securing the adhesive means to the other portion of the cuff so that the cuff is more tightly secured to the wearer than before the adhesive means was removably secured to the other portion of the cuff.

In another aspect of the present invention, a method of making a glove including: a hollow flexible body member having a closed distal end for containing the wearer's fingers, an open proximal end, and a cuff at the open proximal end; adhesive means on a portion of said cuff for allowing the portion of the cuff to be removably secured to other portions of the cuff; and a removable release sheet covering the adhesive means for protecting the adhesive means before time of use, comprising the steps of: (1) forming a glove on a glove form; (2) applying adhesive means on a portion of the cuff while the glove is on the form; (3) pressing a release sheet against the adhesive means so that the release sheet is removably attached to the adhesive means; and (4) stripping the glove from the mold form so that the portion of the body member which is in contact with the mold form is now on the exterior of the glove while the portion of the body member with the adhesive means attached, is now the interior of the glove.

In accordance with the principles of the present invention, a number of advantages are achieved. Primarily, the present invention provides a simple, straight-forward, reliable, easily fabricated disposable glove for medical use and the like having structure for removably securing the cuff portion of a disposable glove on the hand of a wearer during use without the glove being overly tight or difficult to donn properly. The present invention also provides a disposable glove for medical use and the like wherein the fit in the cuff area may be adjusted to suit a wide variety of wrist sizes. The present invention also provides a method of making a glove having structure for securing the cuff portion on the hand of the wearer during use.

DETAILED DESCRIPTION

Figure 1:
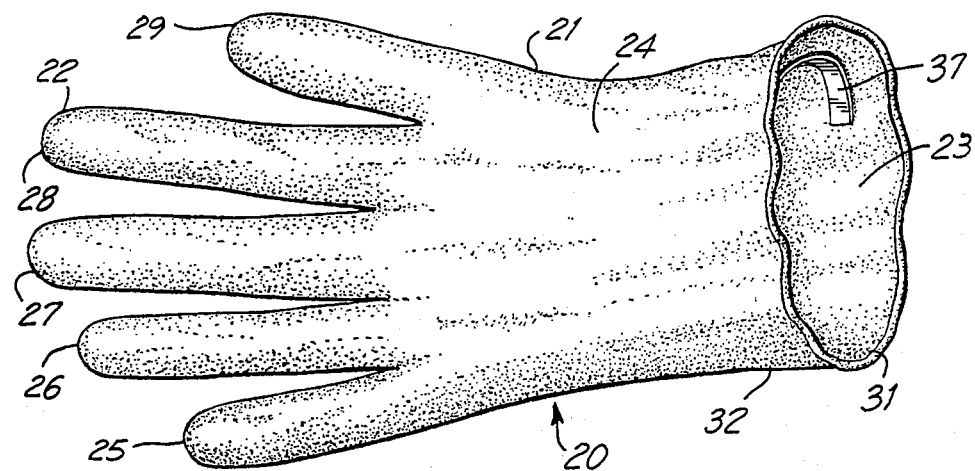
FIG. 1 is a perspective view of a glove of the present invention having improved cuff securing features.

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Figure 2:
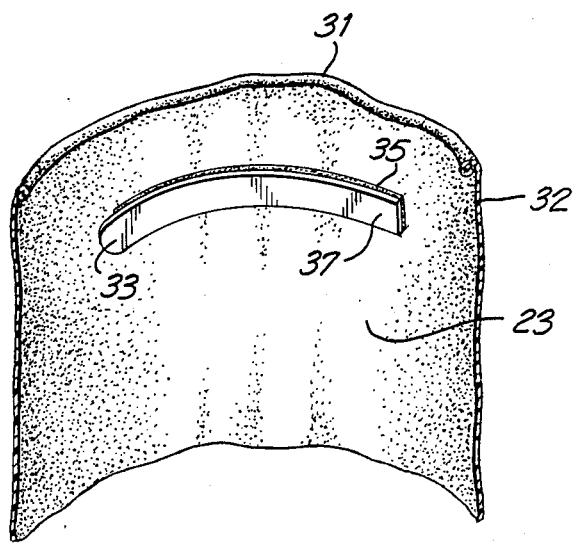
FIG. 2 is a partial cross-sectional view of the glove of FIG. 1 illustrating details of the cuff area.
Figure 3:
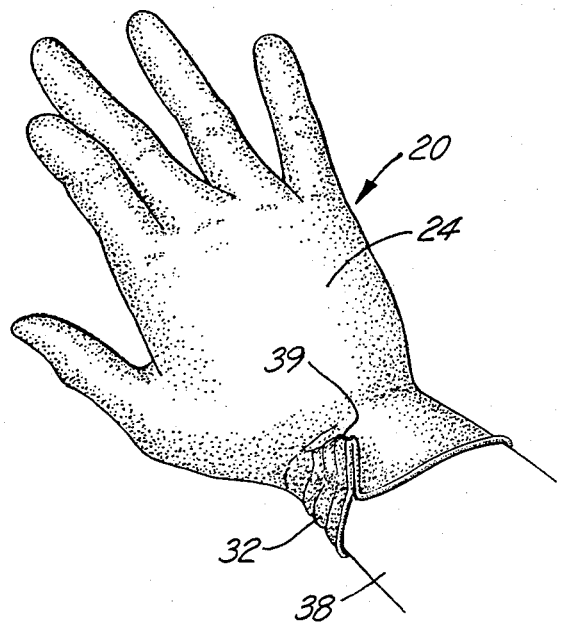
FIG. 3 is a perspective view of the glove of FIG. 1 positioned on the hand of a wearer.

Adverting to FIGS. 1–3, a disposable glove 20, for medical use and the like, includes a hollow flexible body member 21 having an interior surface 23 and an exterior surface 24. Body member 21 includes a closed distal end 22 which in this embodiment is shaped to form five finger-receiving receptacles 25–29, an open proximal end 31 and a cuff 32 at the open proximal end.

For the purposes of the description of the present invention, the term "distal" is generally meant to refer to that end of the glove which is closest to the wearer's fingertips, whereas the term "proximal" is generally meant to refer to the end of the glove closest to the wearer's wrist.

Adhesive means, which in this embodiment, is an elongate strip of adhesive 35 having a major axis substantially parallel to open proximal end 31. As will be explained in more detail hereinafter, adhesive 35 should be formulated so that it will removably attach the portion of the cuff to which it is deposited to another portion of the cuff. A removable release sheet 37 covers adhesive 35 and protects the adhesive before the time of use. Release sheet 37 also includes overhanging gripping tab 33 to facilitate the easy removal of release sheet 37 from adhesive 35 by providing a portion of the release sheet which is easily grasped for removal by the user.

Adhesive 35 is positioned so that when glove 20 is properly positioned on wearer's hand 38 the cuff, with release sheet 37 removed from adhesive 35, may be circumferentially gathered in a direction substantially tangent to the open proximal end causing the adhesive to press against another portion of the cuff removably securing the adhesive to another portion of the cuff so that the cuff, as best illustrated in FIG. 3, is more tightly secured to the wearer than before the adhesive was removably secured to the other portion of the cuff.

It can be seen that the glove of the present invention can provide a snug fit between the cuff of the glove and the user's wrist area for a wide variety of wrist sizes.

This feature is not available in prior art references that use additional elastic means to provide a tighter cuff fit. Use of an elastic means will make the cuff tighter on wearers with larger wrists than on wearers with smaller wrists. This disadvantage is overcome by the instant invention. Further, if the adhesive is formulated for repeated usage, the cuff portion may be readjusted if the original position and/or fit does not prove to be as comfortable or as secure as desired. At the end of the procedure the portions of the cuff which are joined together by the adhesive may be separated thus loosening the cuff fit on the wearer's wrist allowing easy removal of the glove for subsequent disposal.

As best illustrated in FIG. 3, the glove of the present invention eliminates the disadvantages of both a loose cuff and the overly tight cuff which may occur while using gloves without the improved cuff securing features of the present invention. By using the adhesive means on the glove cuff, excess glove material in the cuff area which is folded on itself at 39 to provide a secure fit of the glove cuff to the user's wrists while at the same time accommodating the individual's unique wrist size.

Figure 4:
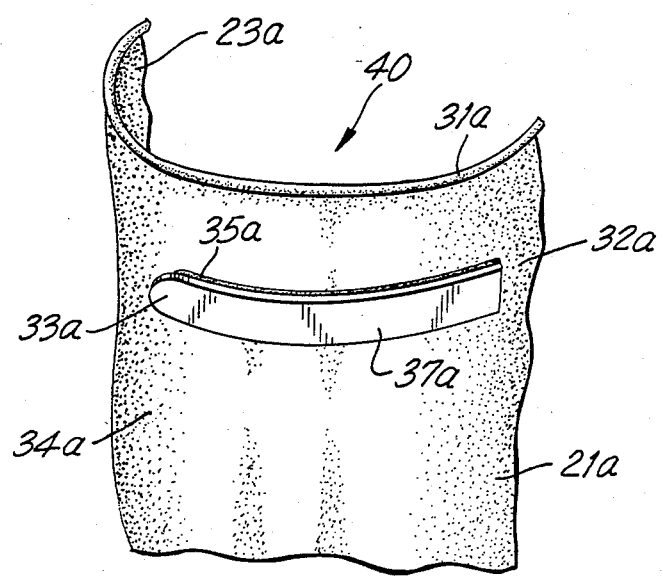
FIG. 4 is a partial cross-sectional view of an alternative embodiment of the present invention wherein the adhesive and backing sheet are on the exterior surface of the cuff.

FIG. 4 illustrates an alternative embodiment of the disposable glove for medical uses and the like of the instant invention. In this alternative embodiment the structure of the glove is substantially similar to the glove of the embodiment of FIGS. 1-3. Accordingly, substantially similar components performing substantially similar functions will be numbered identically to those components in the embodiment of FIGS. 1-3, except a suffix "a" will be used to identify these components in FIG. 4.

A glove 40 includes a hollow flexible body member 21a having an interior surface 23a and an exterior surface 24a. A body member includes a closed distal end (not shown) for containing the wearer's fingers, an open proximal end 31a, and a cuff 32a at the proximal end. Adhesive means, in the form of elongate strip of adhesive 35a having a major axis substantially parallel to open proximal end 31a and spaced from this open proximal end. A removable release sheet 37a covers adhesive 35a for protecting the adhesive before time of use. It should be noted that a release sheet, although preferable, is not absolutely necessary for the instant invention. Various adhesives which are pressure-sensitive or extremely sensitive to contact with itself may provide the function necessary for the removable securing of portions of the cuff without the use of a release sheet to protect the adhesive before time of use. It is within the purview of the instant invention to include adhesive on the interior surface of the cuff and/or the exterior surface of the cuff. The shape and extent of the adhesive are a matter of choice with the elongate strip spaced from the open proximal end of the glove being preferred. It is within the purview of the present invention to use adhesives that are capable of removably attaching to themselves so that the cuff may be secured by causing one portion of the adhesive coated cuff surface to contact another portion of the adhesive coated surface. It is also within the purview of the instant invention to use adhesives which are capable of removably attaching to themselves and to the cuff surface.

Figure 5:
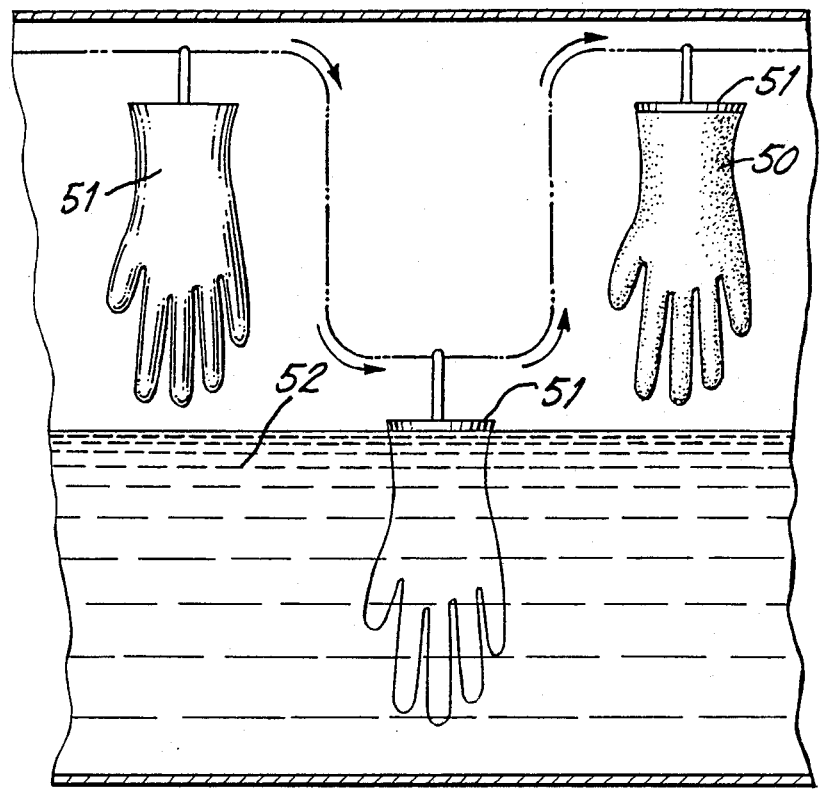
FIG. 5 is a schematic view of a glove forming process using a dip molding method.
Figure 6:
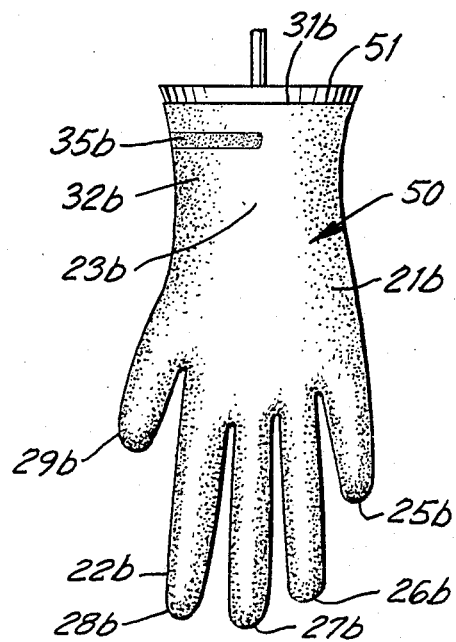
FIG. 6 is a side elevation view illustrating a glove of the present invention still on a mold form with adhesive applied to a portion of the cuff.
Figure 7:
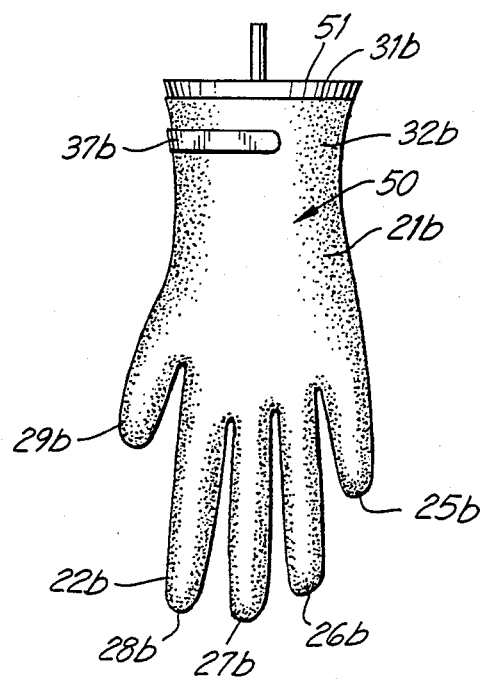
FIG. 7 is a side elevation view illustrating the glove of FIG. 8 on the mold form with a backing sheet attached over the adhesive.
Figure 8:
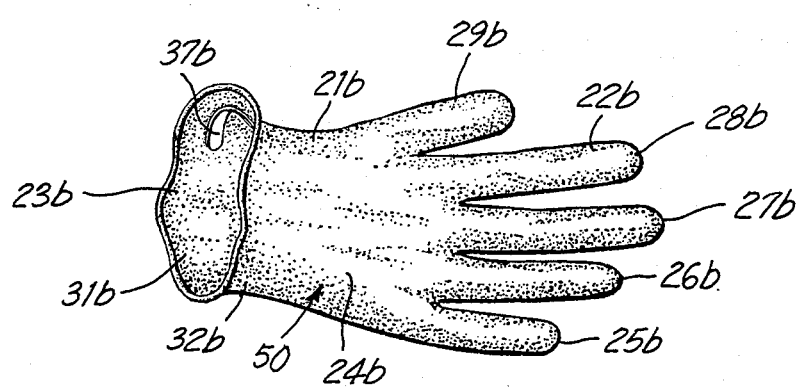
FIG. 8 is a perspective view of the glove of FIG. 7 after being stripped from the mold form.

Adverting to FIGS. 5-8, another aspect of the present invention is a method for producing a glove. The glove produced by the present method is substantially identical to the glove described in FIGS. 1-3. Accordingly, substantially identical components forming substantially identical functions will be numbered identically to those components in the embodiments of FIGS. 1-3, except a suffix "b" will be used to identify these components in FIGS. 5-8. The present invention provides a method of making a glove 50 including: a hollow flexible body member 21b having an interior surface 23b and and exterior surface 24b including a closed distal end 22b which includes finger-receiving receptacles 25b-29b, and open proximal end 31b, and a cuff 32b at the open proximal end; adhesive 35b on a portion of the cuff for allowing that portion of the cuff to be removably secured to other portions of the cuff; and a removable release sheet 37b covering the adhesive for protecting the adhesive before time of use. The method comprises the steps of (1) forming a glove on a glove form 51 (as best illustrated in FIG. 5); (2) applying adhesive 35b on a portion of the cuff while the glove is on mold form 51 wherein the adhesive allowing the portion of the cuff to be removably secured to other portions of the cuff; (3) pressing a release sheet 37b against the adhesive, while the glove is on the mold form, so that the release sheet is removably attached to the adhesive; and (4) stripping the glove from the mold form so that the portion of the body member which was in contact with the mold form is now the exterior surface 24b of the glove while the portion of the body member, with adhesive attached, is now the interior surface 23b of the glove, as best illustrated in FIG. 8.

It is sometimes desirable to have a donning powder such as talcum powder or absorbable corn starch on the interior of the glove to enhance the ease of donning. This donning powder can be applied to the exterior of the glove while the glove is on the mold form, after applying the release sheet to the adhesive, as illustrated in FIG. 7, and before stripping the glove from the mold form so that the donning powder applied to the exterior of the glove while it is on the mold form will be on the interior surface of the glove after it is stripped inside-out off the mold form.

It is within the purview of the present method to include attaching adhesive at various angles and in various shapes at various positions on the cuff including the entire cuff of the glove. The preferred adhesive distribution is the elongated strip having a major axis substantially parallel to the open proximal end of the body member and spaced therefrom. The preferred adhesive distribution is a strip of adhesive approximately three inches long and one-fourth inch wide spaced approximately one inch from the open proximal end of the body member. It is desirable to apply the adhesive to the cuff surface on the portion of the cuff near the thumb receiving portion of the distal end.

It should be noted that in forming the glove as illustrated in FIG. 5, the mold form 51 is dipped into solution 52 so that the mold form is coated by the components of the solution such as latex or plastisol. Plastisol is a dispersion of finely divided resin and a plasticizer. Plastisols are used for molding thermoplastic articles such as gloves. After removal of the glove form from the solution it is usually subject to heat at another station (not shown) to cure or vulcanize the rubber or to fuse the plastic so that the glove will attain its desired properties. Disposable gloves for medical use or the like have an average thickness within the range of approximately about 0.002 inches to 0.005 inches thick. This is an approximate range and it should be noted that various portions of a molded glove such as between the fingers or at the fingertips may be substantially thinner or thicker than portions of the glove formed on the mold where the mold has a larger radius of curvature. Some manufacturers even specify the thickness of the glove based on the thickest portion rather than the average.

The gloves of the present invention may be made of material selected from the group of natural rubber, synthetic rubber, thermoplastic elastomers, thermoplastic, natural rubber latex, synthetic rubber latex and mixes of natural rubber latex and synthetic rubber latex. If a thermoplastic material is selected, plasticized polyvinyl chloride (hereinafter referred to as polyvinyl chloride or vinyl) and polyurethane are preferred materials. It is also within the purview of the instant invention to include gloves which are not molded but are fabricated using parallel layers of flexible thermoplastic films which are heat sealed together along a line which describes a glove shape. For example, a five-finger glove. Portions of the thermoplastic material outside of the heat seal are stripped away leaving a glove which has a heat seal seam running approximately through the center line of all the fingers. Gloves of this type are a very low cost type of glove frequently found in hair care products such as kits for hair color change. The adhesive means of the present invention is ideally suited for this type of low-cost glove.

It is also within the purview of the instant invention to include gloves made of multiple layers bonded together such as a glove made of at least one layer of latex rubber bonded to at least one layer of thermoplastic material. Such multi-layer structures are taught in U.S. Pat. No. 3,382,138 to Barth. In a multi-layer glove structure the preferred materials are at least one layer of latex bonded to at least one layer of polyurethane or polyvinyl chloride.

A wide variety of materials are suitable for adhesive with water-based acrylic adhesives being desirable. Again, the choice of adhesive will depend on the choice of glove material. The adhesive will allow that portion of the cuff to which it is applied to be removably secured to other portions of the cuff preferably several times so that the user may change the cuff fit if the original setting is not proper or becomes uncomfortable or too loose.

A wide variety of materials are suitable for a formulation of the release sheet wherein the choice is primarily determined by the choice of adhesive. Silicone impregnated paper is a desirable release sheet for use with water-based acrylic adhesive.

It is also within the purview of this invention to apply the adhesive to a substrate wherein the substrate may be laminated or sealed to the glove cuff. The substrate will be part of a laminate including the substrate, the adhesive and the release sheet. In this embodiment, the substrate is mounted to the glove cuff using adhesive, ultrasonic welding or other suitable means. The combination of a substrate, adhesive and backing sheet may be purchased in a die cut laminate ready to use from many manufacturers, such as Imperial Marking Systems, Union City, Calif. 94587.

It is sometimes desirable for all of the elements of the glove of the present invention to be sterile when used. When sterility is a requirement, material should also be selected for compatibility with the sterilization process being used.

Thus, it can be seen that the present invention provides a simple, straight-forward, reliable, easily fabricated disposable glove for medical use and the like having structure for securing the cuff portion of the glove on the hand of the wearer during use without the glove being overly tight or difficult to donn properly. The present invention also provides a disposable glove for medical use and the like wherein the fit of the cuff area may be adjusted to suit a wide variety of wrist sizes.

What is claimed is:

1. A glove comprising:
   a hollow flexible body member having an interior surface and an exterior surface, said body member including a closed distal end for containing the wearer's fingers, an open proximal end, and a cuff at said proximal end;
   adhesive means on a tabless portion of said cuff for allowing said portion of said cuff to be removably secured to other portions of said cuff;
   said adhesive means being positioned so that when said glove is properly positioned on the wearer's hand said cuff may be circumferentially gathered in a direction substantially tangent to said open proximal end causing said adhesive means to press against another portion of said cuff removably securing said adhesive means to the other portion of said cuff so that said cuff is more tightly secured to the wearer than before said adhesive means was removably secured to the other portion of said cuff.

2. The glove of claim 1 wherein a portion of said adhesive means is capable of removably attaching to other portions of said adhesive means.

3. The glove of claim 1 wherein a portion of said adhesive means is capable of removably attaching to other portions of said adhesive means and to other portions of said cuff.

4. The glove of claim 1 wherein said adhesive means is an elongate strip having a major axis substantially parallel to said open proximal end.

5. The glove of claim 1 wherein said adhesive means is spaced from said open proximal end.

6. The glove of claim 1 wherein said adhesive means is on said interior surface of said cuff.

7. The glove of claim 1 wherein said closed distal end is shaped to form five finger-receiving receptacles.

8. The glove of claim 1 wherein said adhesive means includes a water-based acrylic adhesive.

9. The glove of claim 1 wherein said adhesive means is covered by a removable release sheet for protecting said adhesive means before time of use.

10. The glove of claim 9 wherein said release sheet is made of silicone impregnated paper.

11. The glove of claim 1 wherein said body member is made of material selected from the group of natural rubber, synthetic rubber, thermoplastic elastomer, thermoplastics, natural rubber latex, synthetic rubber latex and mixtures of natural rubber latex and synthetic rubber latex.

12. The glove of claim 11 wherein said body member is made of thermoplastic material selected from the group of polyvinyl chloride and polyurethane.

13. The glove of claim 1 wherein said body member is made of two layers of flexible thermoplastic films heat sealed together around the periphery of said body portion.

14. The glove of claim 1 wherein said body member is made of at least one layer of latex rubber bonded to at least one layer of a thermoplastic material.

15. The glove of claim 14 wherein said thermoplastic material is selected from the group consisting of polyurethane and polyvinyl chloride.

16. The glove of claim 1 wherein said body member has an average thickness within the range of about 0.002 inches to 0.005 inches.

17. A disposable glove for medical use and the like comprising:
   a closed distal end for containing the wearer's fingers, an open proximal end, and a cuff at said open proximal end;
   adhesive means on a tabless portion of said cuff for allowing said portion of said cuff to be removably secured to other portions of said cuff for tightening said cuff when said glove is on the wearer's hand.

18. A disposable glove for medical use and the like comprising:
   a hollow flexible body member having an interior surface and an exterior surface, said body member including a closed distal end for containing the wearer's fingers, an open proximal end, and a cuff at said open proximal end;
   adhesive means on a tabless portion of said cuff for allowing said portion of said cuff to be removably secured to other portions of said cuff;
   a removable release sheet covering said adhesive means for protecting said adhesive means before time of use;
   said adhesive means being positioned so that when said glove is properly positioned on the wearer's hand said cuff, with release sheet removed from said adhesive means, may be circumferentially gathered in a direction substantially tangent to said open proximal end causing said adhesive means to press against another portion of said cuff removably securing said adhesive means to the other portion of said cuff so that said cuff is more tightly secured to the wearer than before said adhesive means was removably secured to the other portion of said cuff.

19. The glove of claim 18 wherein said adhesive means is on said interior surface of said cuff.

20. The glove of claim 18 wherein a portion of said adhesive means is capable of removably attaching to other portions of said adhesive means.

21. The glove of claim 18 wherein a portion of said adhesive means is capable of removably attaching to other portions of said adhesive means and other portions of said cuff.

22. The glove of claim 18 wherein said body member has an average wall thickness of within the range of about 0.002 to 0.005 inches.

23. The glove of claim 18 wherein said glove is made of a thermoplastic material.

24. A method of making a glove including: a hollow flexible body member having an interior surface and an exterior surface including a closed distal end for containing the wearer's fingers, an open proximal end, and a cuff at said open proximal end; adhesive means on a portion of said cuff for allowing said portion of said cuff to be removably secured to other portions of said cuff; and a removable release sheet covering said adhesive means for protecting said adhesive means before time of use, comprising the steps of:
   (1) forming a glove on a glove form;
   (2) applying adhesive means on a portion of said cuff, while said glove is on the mold form, said adhesive means for allowing said portion of said cuff to be removably secured to other portions of said cuff;
   (3) pressing a release sheet against said adhesive means, while said glove is on the mold form, so that said release sheet is removably attached to said adhesive means; and
   (4) stripping said glove from said mold form so that the portion of said body member which was in contact with the mold form is now the exterior of said glove while the portion of the body member, with adhesive means attached, is now the interior of said glove.

25. The method of claim 24 wherein the said adhesive means and said release sheet are applied to said cuff simultaneously in one step.

26. The method of claim 24 further including the step of applying a donning powder to the glove after the pressing step and before the stripping step.

27. The method of claim 26 wherein the donning powder is absorbable cornstarch.

28. A glove comprising:
   a hollow flexible body member having an interior surface and an exterior surface, said body member including a closed distal end for containing the wearer's fingers, an open proximal end, and a cuff at said proximal end;
   adhesive means on a portion of said interior surface of said cuff for allowing said portion of said cuff to be removably secured to other portions of said cuff;
   said adhesive means being positioned so that when said glove is properly positioned on the wearer's hand said cuff may be circumferentially gathered in a direction substantially tangent to said open proximal end causing said adhesive means to press against another portion of said cuff rmovably securing said adhesive means to the other portion of said cuff so that said cuff is more tightly secured to the wearer than before said adhesive means was removably secured to the other portion of said cuff.

* * * * *